United States Patent
Laughner et al.

(10) Patent No.: US 10,575,900 B2
(45) Date of Patent: Mar. 3, 2020

(54) TISSUE CONTACT SENSING VECTOR

(71) Applicant: Boston Scientific Scimed Inc., Maple Grove, MN (US)

(72) Inventors: Jacob I. Laughner, St. Paul, MN (US); Jason J. Hamann, Blaine, MN (US); Shibaji Shome, Arden Hills, MN (US); Allan C. Shuros, St. Paul, MN (US); Mary M. Byron, Roseville, MN (US); Paul Hultz, Brookline, NH (US); Pramodsingh H. Thakur, Woodbury, MN (US)

(73) Assignee: Boston Scientific Scimed Inc, Maple Grove, MN (US)

( * ) Notice: Subject to any disclaimer, the term of this patent is extended or adjusted under 35 U.S.C. 154(b) by 351 days.

(21) Appl. No.: 15/355,745

(22) Filed: Nov. 18, 2016

(65) Prior Publication Data
US 2017/0143415 A1    May 25, 2017

Related U.S. Application Data

(60) Provisional application No. 62/258,396, filed on Nov. 20, 2015.

(51) Int. Cl.
*A61B 18/12* (2006.01)
*A61B 18/14* (2006.01)
(Continued)

(52) U.S. Cl.
CPC .......... *A61B 18/1492* (2013.01); *A61B 5/044* (2013.01); *A61B 5/04012* (2013.01);
(Continued)

(58) Field of Classification Search
CPC ...... A61B 18/1492; A61B 2018/00083; A61B 2018/00351; A61B 2018/00577;
(Continued)

(56) References Cited

U.S. PATENT DOCUMENTS

| | | |
|---|---|---|
| 5,383,874 A | 1/1995 | Jackson et al. |
| 5,647,870 A | 7/1997 | Kordis et al. |

(Continued)

FOREIGN PATENT DOCUMENTS

| | | |
|---|---|---|
| EP | 2364664 A1 | 9/2011 |
| EP | 2862537 A1 | 4/2015 |

(Continued)

OTHER PUBLICATIONS

International Search Report and Written Opinion issued in PCT/US2016/062847, dated Mar. 2, 2017, 15 pages.

(Continued)

*Primary Examiner* — Michael F Peffley
(74) *Attorney, Agent, or Firm* — Faegre Baker Daniels LLP

(57) ABSTRACT

A catheter system includes a catheter comprising a tip assembly, the tip assembly having a plurality of electrodes and the plurality of electrodes are configured to measure electrical signals. The system also includes a processing unit configured to: receive a first electrical signal sensed by a first electrode of the plurality of electrodes and a second electrical signal sensed by a second electrode of the plurality of electrodes. A first vector is determined based on the first electrical signal that corresponds to the first electrode. A second vector is determined based on the second electrical signal that corresponds to the second electrode. A resultant vector is determined by summing at least the first vector and the second vector, wherein the resultant vector is indicative of the orientation of the tip assembly.

20 Claims, 12 Drawing Sheets

(51) Int. Cl.
*A61B 5/04* (2006.01)
*A61B 5/0408* (2006.01)
*A61B 5/044* (2006.01)
*A61B 5/00* (2006.01)
*A61M 25/01* (2006.01)
*A61B 18/00* (2006.01)

(52) U.S. Cl.
CPC ........ *A61B 5/04085* (2013.01); *A61B 5/4836* (2013.01); *A61M 25/0147* (2013.01); *A61B 2018/00011* (2013.01); *A61B 2018/0072* (2013.01); *A61B 2018/00351* (2013.01); *A61B 2018/00577* (2013.01); *A61B 2018/00839* (2013.01)

(58) Field of Classification Search
CPC ........... A61B 2018/00797; A61B 2018/00839; A61B 2018/00869; A61B 2018/00875; A61B 2018/00892; A61B 2018/1417; A61B 2018/1467; A61B 2018/1597; A61B 2218/002
See application file for complete search history.

(56) References Cited

U.S. PATENT DOCUMENTS

| | | | | |
|---|---|---|---|---|
| 5,755,664 A * | 5/1998 | Rubenstein | ........ | A61N 1/0565 600/377 |
| 5,836,990 A | 11/1998 | Li | | |
| 6,647,281 B2 | 11/2003 | Morency | | |
| 7,633,502 B2 * | 12/2009 | Willis | ........ | A61B 5/0422 345/420 |
| 8,128,617 B2 | 3/2012 | Bencini et al. | | |
| 8,414,579 B2 | 4/2013 | Kim et al. | | |
| 10,098,692 B2 * | 10/2018 | Allison | ........ | A61B 18/1492 |
| 2008/0243214 A1 | 10/2008 | Koblish | | |
| 2008/0275439 A1 * | 11/2008 | Francischelli | ..... | A61B 18/1402 606/34 |
| 2011/0224664 A1 * | 9/2011 | Bar-Tal | ........ | A61B 18/1492 606/33 |
| 2012/0277574 A1 * | 11/2012 | Panescu | ........ | A61B 5/0422 600/421 |
| 2013/0190747 A1 * | 7/2013 | Koblish | ........ | A61B 18/1492 606/33 |
| 2015/0011995 A1 * | 1/2015 | Avitall | ........ | A61B 18/1492 606/46 |

FOREIGN PATENT DOCUMENTS

| | | |
|---|---|---|
| JP | 2009518150 A | 5/2009 |
| JP | 2015506234 A | 3/2015 |
| JP | 2015096193 A | 5/2015 |
| WO | 2013106557 A1 | 7/2013 |
| WO | 2015069887 A1 | 5/2015 |

OTHER PUBLICATIONS

International Preliminary Report on Patentability issued in PCT/US2016/062847, dated May 31, 2018, 10 pages.

* cited by examiner

TISSUE CONTACT SENSING VECTOR

CROSS-REFERENCE TO RELATED APPLICATION

This application claims priority to Provisional Application No. 62/258,396, filed Nov. 20, 2015, which is herein incorporated by reference in its entirety.

TECHNICAL FIELD

Embodiments of the present disclosure relate to medical devices and methods for ablating and/or mapping an anatomical space of a patient's body. More specifically, embodiments of the disclosure relate to devices and methods for determining an orientation of a tip assembly of a catheter positioned within an anatomical space.

BACKGROUND

Aberrant conductive pathways disrupt the normal path of the heart's electrical impulses. For example, conduction blocks can cause the electrical impulse to degenerate into several circular wavelets that disrupt the normal activation of the atria or ventricles. The aberrant conductive pathways create abnormal, irregular, and sometimes life-threatening heart rhythms called arrhythmias. Ablation is one way of treating arrhythmias and restoring normal conduction. The sources of the aberrant pathways (called focal arrhythmia substrates) are located or mapped using mapping electrodes situated in a desired location. After mapping, the physician may ablate the aberrant tissue. In radio frequency (RF) ablation, RF energy is directed from the ablation electrode through tissue to an electrode to ablate the tissue and form a lesion.

SUMMARY

When ablating tissue using an ablation electrode, determining the orientation of the catheter tip assembly may be useful to the physician that is performing the ablation. Embodiments of the subject matter disclosed herein include devices and methods for determining an orientation of a tip assembly of a catheter positioned within an anatomical space. In embodiments, a processing device may be configured to implement one or more algorithms to determine an orientation of a tip assembly of a catheter positioned within an anatomical space. In this manner, embodiments of the disclosure may facilitate enhancing the safety and/or effectiveness of performing ablation on a patient. Exemplary embodiments include the following.

In Example 1, a catheter system comprises a catheter comprising a tip assembly, the tip assembly having a plurality of electrodes, the plurality of electrodes configured to measure electrical signals; and a processing unit configured to: receive a first electrical signal sensed by a first electrode of the plurality of electrodes and a second electrical signal sensed by a second electrode of the plurality of electrodes; determine a first vector, based on the first electrical signal, corresponding to the first electrode; determine a second vector, based on the second electrical signal, corresponding to the second electrode; and determine a resultant vector by summing at least the first vector and the second vector, wherein the resultant vector is indicative of the orientation of the tip assembly.

In Example 2, the catheter system of Example 1, the processing unit further configured to cause the first and second electrodes to provide a first and second current into a patient's body, respectively.

In Example 3, the catheter system of any of Examples 1 and 2, the first vector comprising a first magnitude and a first direction, and the second vector comprising a second magnitude and a second direction, wherein the first and second directions correspond, respectively, to a first and second position relative to a central terminal.

In Example 4, the catheter system of Example 3, wherein the first and second magnitudes comprise a first and second voltage, respectively.

In Example 5, the catheter system of any of Examples 1 through 4, further comprising a display device operatively coupled to the processing unit, wherein the processing unit is configured to cause the display device to present a representation of the orientation of the tip assembly.

In Example 6, the catheter system of Example 5, wherein the representation of the orientation of the tip assembly comprises a graphical depiction of the resultant vector.

In Example 7, the catheter system of any of Examples 1 through 6, the tip assembly further comprising an exterior wall configured to deliver radio frequency (RF) energy for an RF ablation procedure, the plurality of electrodes comprising a plurality of mapping electrodes evenly distributed along a circumference of the exterior wall.

In Example 8, an ablation catheter system comprises a catheter comprising: a tip assembly that includes a conductive exterior wall for delivering radio frequency (RF) energy for an RF ablation procedure, and a plurality of mapping electrode openings; and a plurality of mapping electrodes, positioned in the plurality of mapping electrode openings, the plurality of mapping electrodes configured to measure electrical signals; and a processing unit configured to: drive a first current through a first mapping electrode of the plurality of mapping electrodes and a second current through a second mapping electrode of the plurality of mapping electrodes; receive a first electrical signal sensed by the first mapping electrode and a second electrical signal sensed by the second mapping electrode; determine a first vector, based on the first electrical signal, corresponding to the first mapping electrode; determine a second vector, based on the second electrical signal, corresponding to the second mapping electrode; and determine a resultant vector by summing at least the first vector and the second vector, wherein the resultant vector is indicative of the orientation of the tip assembly.

In Example 9, the ablation catheter system of Example 8, the first vector comprising a first magnitude and a first direction, and the second vector comprising a second magnitude and a second direction, wherein the first and second directions correspond, respectively, to a first and second position relative to a central terminal.

In Example 10, the ablation catheter system of Example 9, wherein the first and second magnitudes comprise a first and second voltage, respectively.

In Example 11, the ablation catheter system of Example 9, wherein the first and second magnitudes comprise a first and second impedance, respectively.

In Example 12, the ablation catheter system of any of Examples 8 through 11, further comprising a display device operatively coupled to the processing unit, wherein the processing unit is configured to cause the display device to present a representation of the orientation of the tip assembly.

In Example 13, a method of determining an orientation of a tip assembly of an ablation catheter, the tip assembly comprising a conductive exterior wall configured to deliver radio frequency (RF) energy for an RF ablation procedure, and a plurality of mapping electrodes evenly distributed along a circumference of the exterior wall, the method comprising: receiving a first electrical signal from a first mapping electrode of the plurality of mapping electrodes; receiving a second electrical signal from a second mapping electrode of the plurality of mapping electrodes; determining a first vector, based on the first electrical signal, corresponding to the first mapping electrode; determining a second vector, based on the second electrical signal, corresponding to the second mapping electrode; determining a resultant vector by summing at least the first vector and the second vector, wherein the resultant vector is indicative of an orientation of the tip assembly; and causing a display device to present a representation of the orientation of the tip assembly.

In Example 14, the method of Example 13, wherein the representation of the orientation of the tip assembly comprises a graphical depiction of the resultant vector.

In Example 15, the method of any of Examples 13 and 14, wherein determining the first vector and the second vector comprises determining a first magnitude and a first direction, and a second magnitude and a second direction, respectively, wherein the first and second directions correspond, respectively, to a first and second position relative to a central terminal.

In Example 16, a catheter system comprises a catheter comprising a tip assembly, the tip assembly having a plurality of electrodes, the plurality of electrodes configured to measure electrical signals; and a processing unit configured to: receive a first electrical signal sensed by a first electrode of the plurality of electrodes and a second electrical signal sensed by a second electrode of the plurality of electrodes; determine a first vector, based on the first electrical signal, corresponding to the first electrode; determine a second vector, based on the second electrical signal, corresponding to the second electrode; and determine a resultant vector by summing at least the first vector and the second vector, wherein the resultant vector is indicative of the orientation of the tip assembly.

In Example 17, the catheter system of Example 16, the processing unit further configured to cause the first and second electrodes to provide a first and second current into a patient's body, respectively.

In Example 18, the catheter system of Example 16, the first vector comprising a first magnitude and a first direction, and the second vector comprising a second magnitude and a second direction, wherein the first and second directions correspond, respectively, to a first and second position relative to a central terminal.

In Example 19, the catheter system of Example 18, wherein the first and second magnitudes comprise a first and second voltage, respectively.

In Example 20, the catheter system of Example 16, further comprising a display device operatively coupled to the processing unit, wherein the processing unit is configured to cause the display device to present a representation of the orientation of the tip assembly.

In Example 21, the catheter system of Example 20, wherein the representation of the orientation of the tip assembly comprises a graphical depiction of the resultant vector.

In Example 22, the catheter system of Example 16, the tip assembly further comprising an exterior wall configured to deliver radio frequency (RF) energy for an RF ablation procedure, the plurality of electrodes comprising a plurality of mapping electrodes evenly distributed along a circumference of the exterior wall.

In Example 23, an ablation catheter system comprises a catheter comprising: a tip assembly that includes a conductive exterior wall for delivering radio frequency (RF) energy for an RF ablation procedure, and a plurality of mapping electrode openings; and a plurality of mapping electrodes, positioned in the plurality of mapping electrode openings, the plurality of mapping electrodes configured to measure electrical signals; and a processing unit configured to: drive a first current through a first mapping electrode of the plurality of mapping electrodes and a second current through a second mapping electrode of the plurality of mapping electrodes; receive a first electrical signal sensed by the first mapping electrode and a second electrical signal sensed by the second mapping electrode; determine a first vector, based on the first electrical signal, corresponding to the first mapping electrode; determine a second vector, based on the second electrical signal, corresponding to the second mapping electrode; and determine a resultant vector by summing at least the first vector and the second vector, wherein the resultant vector is indicative of the orientation of the tip assembly.

In Example 24, the ablation catheter system of Example 23, the first vector comprising a first magnitude and a first direction, and the second vector comprising a second magnitude and a second direction, wherein the first and second directions correspond, respectively, to a first and second position relative to a central terminal.

In Example 25, the ablation catheter system of Example 24, wherein the central terminal comprises a virtual electrode that represents a vector summation based on vectors associated with all of the plurality of mapping electrodes.

In Example 26, the ablation catheter system of Example 24, wherein the first and second magnitudes comprise a first and second voltage, respectively.

In Example 27, the ablation catheter system of Example 24, wherein the first and second magnitudes comprise a first and second impedance, respectively.

In Example 28, the ablation catheter system of Example 23, further comprising a display device operatively coupled to the processing unit, wherein the processing unit is configured to cause the display device to present a representation of the orientation of the tip assembly.

In Example 29, the ablation catheter system of Example 28, wherein the representation of the orientation of the tip assembly comprises a graphical depiction of the resultant vector.

In Example 30, a method of determining an orientation of a tip assembly of an ablation catheter, the tip assembly comprising a conductive exterior wall configured to deliver radio frequency (RF) energy for an RF ablation procedure, and a plurality of mapping electrodes evenly distributed along a circumference of the exterior wall, the method comprising: driving a first current through a first mapping electrode of the plurality of mapping electrodes; driving a second current through a second mapping electrode of the plurality of mapping electrodes; receiving a first electrical signal sensed by the first mapping electrode; receiving a second electrical signal sensed by the second mapping electrode; determining a first vector, based on the first electrical signal, corresponding to the first mapping electrode; determining a second vector, based on the second electrical signal, corresponding to the second mapping electrode; determining a resultant vector by summing at least the first vector and the second vector, wherein the resultant vector is indicative of an orientation of the tip assembly; and causing a display device to present a representation of the orientation of the tip assembly.

In Example 31, the method of Example 30, wherein the representation of the orientation of the tip assembly comprises a graphical depiction of the resultant vector.

In Example 32, the method of Example 30, wherein determining the first vector and the second vector comprises determining a first magnitude and a first direction, and a second magnitude and a second direction, respectively, wherein the first and second directions correspond, respectively, to a first and second position relative to a central terminal.

In Example 33, the method of Example 32, wherein the first and second magnitudes comprise a first and second voltage, respectively.

In Example 34, the method of Example 32, wherein the central terminal comprises a virtual electrode that represents a vector summation based on vectors associated with all of the plurality of mapping electrodes.

In Example 35, the method of Example 32, further comprising driving RF energy through the exterior wall for an RF ablation procedure; and filtering the first and second electrical signals to remove an RF component from each.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

Figures 1, 2:
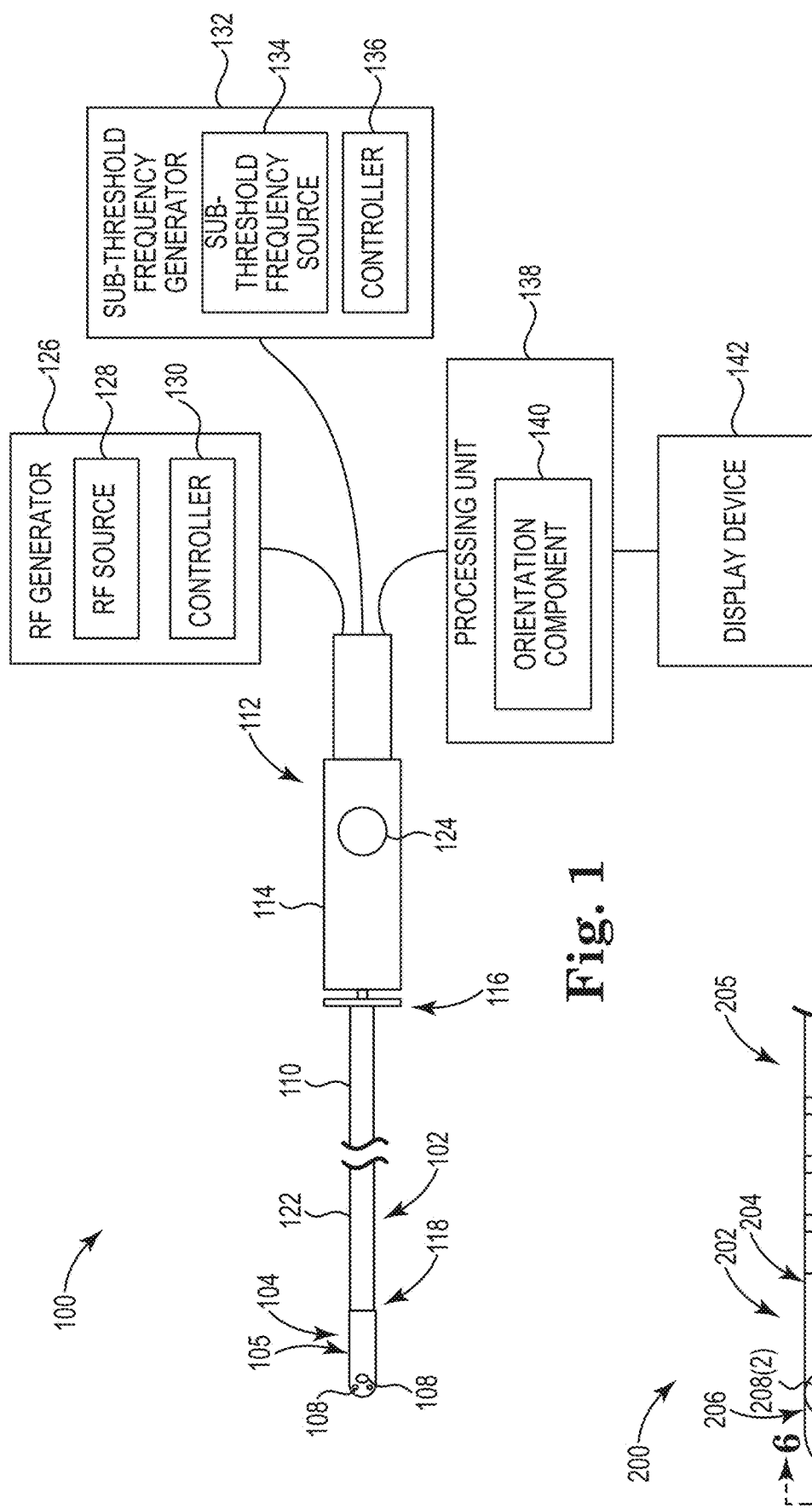
FIG. 1 depicts an illustrative mapping and ablation system that includes a catheter having mapping electrodes, in accordance with embodiments of the disclosure.
FIG. 2 depicts an illustrative tip assembly for a mapping and ablation catheter, in accordance with embodiments of the disclosure.

While the disclosed subject matter is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

As the terms are used herein with respect to ranges of measurements (such as those disclosed immediately above), "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error, differences in measurement and/or manufacturing equipment calibration, human error in reading and/or setting measurements, adjustments made to optimize performance and/or structural parameters in view of differences in measurements associated with other components, particular implementation scenarios, imprecise adjustment and/or manipulation of objects by a person or machine, and/or the like.

Although the term "block" may be used herein to connote different elements illustratively employed, the term should not be interpreted as implying any requirement of, or particular order among or between, various steps disclosed herein unless and except when explicitly referring to the order of individual steps.

DETAILED DESCRIPTION

Embodiments of the disclosure relate to a radiofrequency (RF) ablation catheter system. In embodiments, the catheter may be a hybrid catheter, which may be configured to be used for both localized mapping and ablation functions. The hybrid catheter may be configured to provide localized, high resolution ECG signals during ablation. This localized mapping may enable the ablation procedure to be more precise than that which can be achieved with conventional, non-hybrid ablation catheters. The catheter may be irrigated and may have a closed-irrigated catheter design, or an open-irrigated catheter design. That is, for example, a cooling fluid, such as a saline, may be delivered through the catheter to a tip assembly having a tissue ablation electrode, where the fluid circulates therein and/or exits through irrigation ports defined in the tissue ablation electrode to cool the electrode and surrounding tissue during ablation. Additionally, the tip assembly may include one or more mapping electrodes so that the localized intra cardiac electrical activity can be recorded in real time or near-real time at the location of energy delivery.

FIG. 1 depicts a mapping and ablation system 100 that includes an open-irrigated ablation catheter 102, according to embodiments of the disclosure. The illustrated catheter 102 includes a tip assembly 104 having a tissue ablation electrode 105, with mapping electrodes 106, and distal irrigation ports 108. In embodiments, the catheter 102 may be a closed-irrigated catheter or a non-irrigated catheter. The catheter 102 includes a catheter body 110 and a proximal catheter handle assembly 112, having a handle 114, coupled to a proximal end 116 of the catheter body 110. The tip assembly 104 is coupled to a distal end 118 of the catheter body 110.

In some instances, the mapping and ablation system 100 may be utilized in ablation procedures on a patient and/or in ablation procedures on other objects. In various embodiments, the ablation catheter 102 may be configured to be introduced into or through the vasculature of a patient and/or into or through any other lumen or cavity. In an example, the ablation catheter 102 may be inserted through the vasculature of the patient and into one or more chambers of the patient's heart (e.g., a target area). When in the patient's vasculature or heart, the ablation catheter 102 may be used to map and/or ablate myocardial tissue using the electrodes 106 and/or the tissue ablation electrode 105. In embodiments, the tissue ablation electrode 105 may be configured to apply ablation energy to myocardial tissue of the heart of a patient.

According to embodiments, the tissue ablation electrode 105 may be, or be similar to, any number of different tissue ablation electrodes such as, for example, the IntellaTip MiFi,™ Orion™ or the Blazer™ Ablation tip, both of which are available from Boston Scientific of Marlborough, Mass. In embodiments, the tissue ablation electrode 105 may have any number of different sizes, shapes, and/or other configuration characteristics. The tissue ablation electrode 105 may be any length and may have any number of the electrodes 106 positioned therein and spaced circumferentially and/or longitudinally about the tissue ablation electrode 105. In some instances, the tissue ablation electrode 105 may have a length of between one (1) mm and twenty (20) mm, three (3) mm and seventeen (17) mm, or six (6) mm and fourteen (14) mm. In an illustrative example, the tissue ablation electrode 105 may have an axial length of about eight (8) mm. In another illustrative example, the tissue ablation electrode 105 may include an overall length of approximately 4-10 mm. In embodiments, the tissue ablation electrode 105 may include an overall length of approximately 4 mm, 4.5 mm, and/or any other desirable length. In some cases, the plurality of electrodes 106 may be spaced at any interval about the circumference of the tissue ablation electrode 105. In an example, the tissue ablation electrode 105 may include at least three electrodes 106 equally or otherwise spaced about the circumference of the tissue ablation electrode 105 and at the same or different longitudinal positions along the longitudinal axis of the tissue ablation electrode 105.

In embodiments, the catheter 102 may include a deflectable catheter region 122 configured to allow the catheter 102 to be steered through the vasculature of a patient, and which may enable the tissue ablation electrode 105 to be accurately placed adjacent a targeted tissue region. A steering wire (not shown) may be slidably disposed within the catheter body 110. The handle assembly 112 may include one or more steering members 124 such as, for example, rotating steering knobs that are rotatably mounted to the handle 114. Rotational movement of a steering knob 124 relative to the handle 114 in a first direction may cause a steering wire to move proximally relative to the catheter body 110 which, in turn, may tension the steering wire, thus pulling and bending the catheter deflectable region 122 into an arc; and rotational movement of the steering knob 124 relative to the handle 114 in a second direction may cause the steering wire to move distally relative to the catheter body 110 which, in turn, may relax the steering wire, thus allowing the catheter 102 to return toward its original form. To assist in the deflection of the catheter 102, the deflectable catheter region 122 may be made of a lower durometer plastic than the remainder of the catheter body 110.

According to embodiments, the catheter body 110 includes one or more cooling fluid lumens (not shown) and may include other tubular element(s) to provide desired functionality to the catheter 102. The addition of metal in the form of a braided mesh layer sandwiched in between layers of plastic tubing may be used to increase the rotational stiffness of the catheter 102.

The illustrated system 100 includes an RF generator 126 used to generate RF energy for use during an ablation procedure. The RF generator 126 may include an RF source 128 that produces the RF energy and a controller 130 for controlling the timing, level, and/or other characteristics of the RF energy delivered through the tip assembly 104. The RF generator 126 may be configured to deliver ablation energy to the ablation catheter 102 in a controlled manner in order to ablate the target tissue sites. Ablation of tissue within the heart is well known in the art, and thus for purposes of brevity, the RF generator 126 will not be described in further detail. Further details regarding RF generators are provided in U.S. Pat. No. 5,383,874, which is expressly incorporated herein by reference in its entirety for all purposes.

The illustrated system 100 includes a sub-threshold frequency generator 132 used to generate energy for determining tissue impedance. The sub-threshold frequency generator 132 may include a sub-threshold frequency source 134 that produces sub-threshold energy and a controller 134 for controlling the timing, level, and/or other characteristics of the sub-threshold frequency energy delivered through the tip assembly 104. The sub-threshold frequency generator 132 may be configured to deliver energy to tip assembly 104 in a controlled manner in order to determine tissue impedance, as described in more detail below, but at a frequency that is below an ablation frequency. In embodiments, the sub-ablation frequency may be on the order of 10 kHz; however, this is only an example and not meant to be limiting.

The illustrated system 100 also includes a fluid source (not shown), for providing cooling fluid, such as a saline, through the catheter 102 and out through the irrigation ports 108. A processing unit 138 may be connected to the electrodes 106. The processing unit 138 and electrodes 106 may be configured to detect electrical activity of the heart. This electrical activity may be evaluated to analyze an arrhythmia and to determine where to deliver the ablation energy as a therapy for the arrhythmia. Although the processing unit 138, RF generator 126 and secondary-frequency generator 138 are shown as discrete components, they can alternatively be incorporated into a single integrated device.

The processing unit 138 may include an orientation component 140 configured to determine, based on electrical signals sensed by the electrodes 106, an orientation of the tip assembly 104. Additionally, the processing unit 138 may be operatively coupled to a display device 142 and may be configured to cause the display device 142 to present a representation of the orientation of the tip assembly 104. For example, in embodiments, the orientation component 140 may determine a relative orientation of the tip assembly 104, relative to anatomical tissue (e.g., cardiac tissue). The representation of the orientation of the tip assembly 104 may include, for example, a graphical depiction of a vector such as, for example, a resultant vector determined by summing a plurality of vectors corresponding to the electrodes 106, as described in more detail below.

One of ordinary skill in the art will understand that various components such as, for example, aspects of the RF generator 126, the processing unit 138, the orientation component 140, and/or the display device 142, may be implemented using software, hardware, and/or firmware. Various methods of operation may be implemented as a set of instructions contained on a computer-accessible medium capable of directing a processor to perform the respective method.

The RF ablation catheter 102 as described may be used to perform various diagnostic functions to assist the physician in an ablation treatment. For example, in some embodiments, the catheter 102 may be used to ablate cardiac arrhythmias, and at the same time provide real-time assessment of a lesion formed during RF ablation. Real-time assessment of the lesion may involve any of monitoring surface and/or tissue temperature at or around the lesion, reduction in the electrocardiogram signal, a drop in impedance, direct and/or surface visualization of the lesion site, and imaging of the tissue site (e.g., using computed tomography, magnetic resonance imaging, ultrasound, etc.). In addition, the presence of the electrodes within the RF tip electrode can operate to assist the physician in locating and positioning the tip electrode at the desired treatment site, and to determine the position and orientation of the tip electrode relative to the tissue to be ablated.

Illustrative catheters that may be used as the catheter 102 may include, among other ablation and/or mapping catheters, those described in U.S. patent application Ser. No. 12/056,210 filed on Mar. 26, 2008, and entitled HIGH RESOLUTION ELECTROPHYSIOLOGY CATHETER, and U.S. Pat. No. 8,414,579 filed on Jun. 23, 2010, entitled MAP AND ABLATE OPEN IRRIGATED HYBRID CATHETER, which are both hereby incorporated herein by reference in their entireties for all purposes. Alternatively, or in addition, catheters that may be used as the catheter 102 may include, among other ablation and/or mapping catheters, those described in U.S. Pat. No. 5,647,870 filed on Jan. 16, 1996, as a continuation of U.S. Ser. No. 08/206,414, filed Mar. 4, 1994 as a continuation-in-part of U.S. Ser. No. 08/33,640, filed Mar. 16, 1993, entitled MULTIPLE ELECTRODE SUPPORT STRUCTURES, U.S. Pat. No. 6,647,281 filed on Apr. 6, 2001, entitled EXPANDABLE DIAGNOSTIC OR THERAPEUTIC APPARATUS AND SYSTEM FOR INTRODUCING THE SAME INTO THE BODY, and U.S. Pat. No. 8,128,617 filed on May 27, 2008, entitled ELECTRICAL MAPPING AND CRYO ABLATING WITH A BALLOON CATHETER, which are all hereby incorporated herein by reference in their entireties for all purposes.

FIG. 2 illustrates a hybrid catheter 200, according to embodiments of the disclosure, having three electrodes used to perform a mapping function and/or to determine an orientation of the tip assembly of the hybrid catheter. The illustrated catheter 200 includes a tip assembly 202 coupled to a distal end of a catheter body 205, having a tip body 204, and an ablation electrode 206 used to perform mapping and ablation functions. In embodiments, the ablation functions may be performed, in part, by the ablation electrode 206, which may function as an RF electrode. The mapping functions may be performed, at least in part, by mapping electrodes 208 and mapping ring electrodes 212.

The illustrated tip assembly 202 includes a generally hollow ablation electrode 206 having an open interior region defined by an exterior wall 210 of the tip assembly 202. In the illustrated embodiments, the hollow tip body 204 has a generally cylindrical shape, but in other embodiments, the tip body 204 may have any number of different shapes such as, for example, an elliptical shape, a polygonal shape, and/or the like. By way of an example and not limitation, embodiments of the tip assembly 202 may have a diameter on the order of about 0.08-0.1 inches, a length on the order of about 0.2-0.3 inches, and an exterior wall 210 with a thickness on the order of about 0.003-0.004 inches. According to embodiments, the ablation electrode 206 may be formed from a conductive material. For example, some embodiments use a platinum-iridium alloy. Some embodiments use an alloy with approximately 90% platinum and 10% iridium. The conductive material of the ablation electrode 206 is used to conduct RF energy used to form legions during the ablation procedure.

Figure 3A:
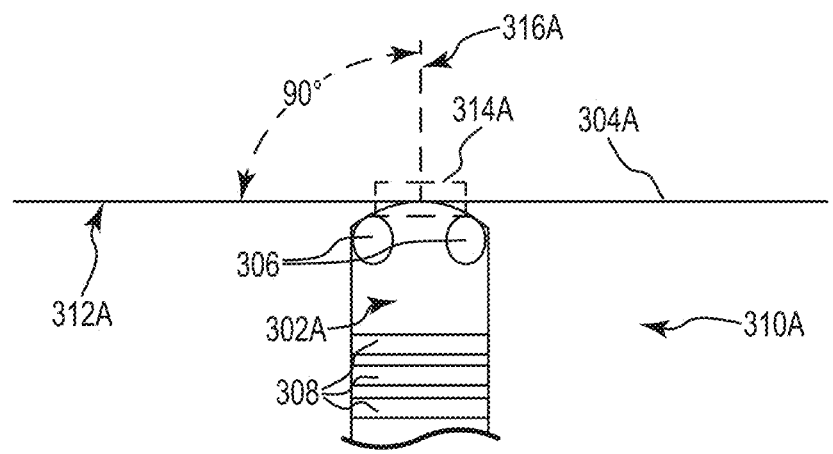
FIGS. 3A-3C depict three types of orientations of catheter tip assemblies with respect to cardiac tissue, in accordance with embodiments of the disclosure.
Figure 3B:
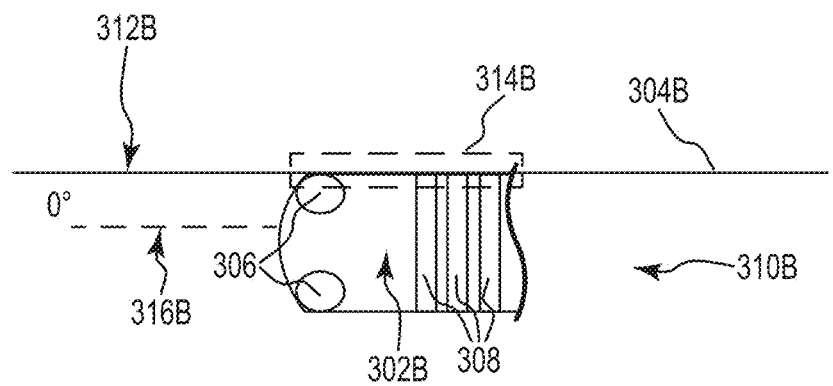
Figure 3C:
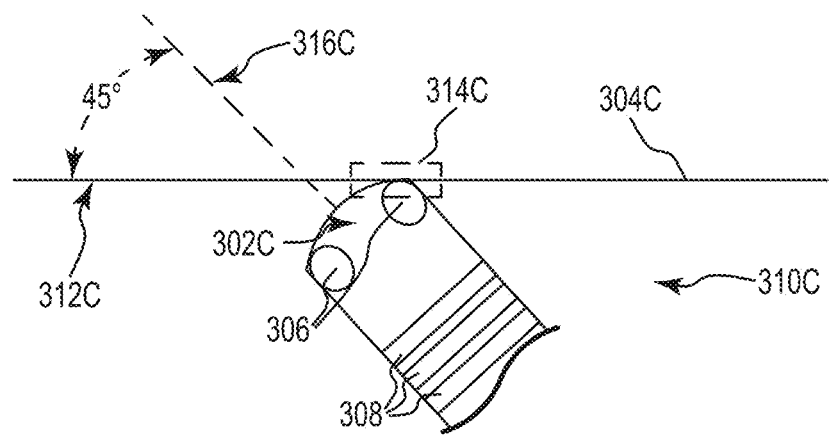

As stated above, the orientation of the tip assembly 202 in relation to cardiac tissue may be determined. FIGS. 3A-3C depict three types of orientations of catheter tip assemblies 302A-302C with respect to cardiac tissue 304A-304C. A catheter tip assembly can have different orientations with respect to the surface of cardiac tissue 304A-304C than are depicted in FIGS. 3A-3C. As such, FIGS. 3A-3C are not meant to be limiting in scope, but instead, are shown for illustrative purposes.

In the embodiments shown in FIGS. 3A-3C, the catheter tip assemblies 302A-302C may have some or all of the functionality of the catheter tip assemblies 104, 202 shown in FIGS. 1 and 2, respectively. In particular, the catheter tip assemblies 302A-302C may be configured to perform mapping and ablation functions, as described above. Furthermore, the catheter tip assemblies 302A-302C may have mapping electrodes 308 and/or mapping ring electrodes 310 disposed thereon.

Referring to FIG. 3A, the catheter tip assembly 302A, which is disposed in a blood pool 310A and contacting the surface 312A of the cardiac tissue 304A at a contact region 314A, may have a sub-optimal orientation with respect to the surface 312A of cardiac tissue 304A. In particular, the angle between a normal 316A to the catheter tip assembly 302A and the surface 312A of the cardiac tissue 304A is 90 degrees. Typically, when a tip assembly 302A has this orientation, or approximately this orientation, with respect to a surface 312A of cardiac tissue 304A, pressure applied to the catheter tip assembly 302A, by a user, may translate into pressure being directly applied into the cardiac tissue 304A. As such, if a user of the catheter tip assembly 302A is ablating a portion of the cardiac tissue 304A and either applies to much pressure to the catheter tip assembly 302A or ablates the cardiac tissue 304A for too long, the catheter tip assembly 302A may perforate the cardiac tissue 304A. As such, a user may want to orient the catheter tip assembly 302A differently than the orientation depicted in FIG. 3A.

Furthermore, when the catheter tip assembly 302A has the orientation, or approximately the orientation, shown in FIG. 3A, the electrodes 306, 308 may sense a voltage that corresponds more to a blood pool 310A than the tissue 304A because the electrodes 306, 308 are not part of the contact region 314A that is contacting the cardiac surface 312A. As such, the sensed voltage may be relatively small because cardiac tissue has a higher impedance than blood, as understood by those having skill in the art. According to embodiments, this sensed voltage is used to determine a resultant vector and the orientation of the catheter tip assembly, as described below.

Referring to FIG. 3B, the catheter tip assembly 302B, which is disposed in a blood pool 310B and contacting the surface 312B of the cardiac tissue 304B at a contact region 314B, may also have a sub-optimal orientation with respect to the surface 312B of cardiac tissue 304B. In particular, the angle between a normal 316B to the catheter tip assembly 302B and the surface 312B of the cardiac tissue 304B is 0 degrees. When a catheter assembly 302B has this orientation, or approximately this orientation, with respect to a surface 312B of cardiac tissue 304B, a user may be more likely to unintentionally move the catheter tip assembly 302B with respect to the cardiac tissue 304B, if the user applies pressure to the catheter tip assembly 302A. As such, a portion of the surface 312B of the cardiac tissue 304B may be ablated that was not intended to be ablated. Additionally, when a catheter tip assembly 302B has the orientation, or approximately the orientation, depicted in FIG. 3B, the contact region 314B is larger than when a catheter tip assembly 302B has other orientations. As such, a user may ablate a larger portion of the surface 312B of the cardiac tissue 304B than was intended. Accordingly, a user may want to orient the catheter tip assembly 302B differently than the orientation depicted in FIG. 3B.

Furthermore, when the catheter tip assembly 302B has the orientation, or approximately the orientation, shown in FIG. 3B, one or more of the electrodes 306 may sense a voltage that corresponds more to cardiac tissue 304B than the blood pool 310B because one or more of the electrodes 306 are included in the contact region 314B. The number of electrodes 306 that are included in the contact region 314B depends on the orientation of the electrodes 306 on the catheter tip assembly 302B, the orientation of the catheter tip assembly 302B, and how many electrodes 306 are included on the catheter tip assembly 302B. Furthermore, the ring electrodes 308 may also sense a voltage corresponding to the cardiac tissue 304B since the ring electrodes 308 have at least a portion included in the contact region 314B. As such, the voltages sensed by one or more of the electrodes 306 and the electrodes 308 may be relatively large because, as described below, cardiac tissue has a higher impedance than blood. According to embodiments, this sensed voltage is used to determine a resultant vector and the orientation of the catheter tip assembly 302B, as described below.

Referring to FIG. 3C, the catheter tip assembly 302C, which is disposed in a blood pool 310C and contacting the surface 312C of the cardiac tissue 304C at a contact region 314C, may have a more optimal orientation with respect to the surface 312C of cardiac tissue 304C than the orientations shown in FIGS. 3A and 3B. In particular, the angle between a normal 316C to the catheter tip assembly 302C and the surface 312C of the cardiac tissue 304C is 45 degrees. When a catheter tip assembly 302C has this orientation, or approximately this orientation, with respect to a surface 312C of cardiac tissue 304C, pressure applied to the catheter tip assembly 302C, by a user, may not translate into pressure being directly applied into the cardiac tissue 304C. As such, if a user of the catheter tip assembly 302C is ablating a portion of the cardiac tissue 304C and applies too much pressure to the catheter tip assembly 302C, the catheter tip assembly 302C may move with respect to the cardiac tissue 304C. While a different portion of the surface 312C of the cardiac structure 304C may be ablated than was intended, the movement of the catheter tip assembly 302C may prevent the catheter tip assembly 302C from perforating the cardiac structure 304C, which may be better a result than ablating a different portion of the surface 312C of the cardiac structure 304C than was intended. As such, the orientation depicted in FIG. 3C may be better than the orientation depicted in FIG. 3A.

Additionally, when a catheter tip assembly 302C has the orientation, or approximately the orientation, depicted in FIG. 3C, the contact region 314C is smaller than when a catheter tip assembly has the orientation depicted in FIG. 3B. As such, a smaller more targeted portion may be ablated than what is possible with the orientation depicted in FIG. 3B. Furthermore, the catheter tip assembly 302C is less likely to move with respect to the cardiac tissue 304C than the orientation depicted in FIG. 3B since pressure applied to the catheter tip assembly 302C may partially translate into pressure being applied into the cardiac tissue 304C. Accordingly, a user may want to orient a catheter tip assembly 302C as depicted in FIG. 3C. As such, being able to determine the orientation of a catheter tip assembly may be advantageous.

Furthermore, when the catheter tip assembly 302C has the orientation, or approximately the orientation, shown in FIG. 3C, one or more of the electrodes 306 may sense a voltage that corresponds more to the cardiac tissue 304C than the blood pool 310C because one or more of the electrodes 306 are included in the contact region 314C. The number of electrodes 306 that are included in the contact region 314C depends on the orientation of the electrodes 306 around the catheter tip assembly 302C, the orientation of the catheter tip assembly 302C, and how many electrodes 306 are included on the catheter tip assembly 302C. While one or more of the electrodes 306 are included in the contact region 314C, one or more of the electrodes 306 may sense a voltage that is lower than the voltage sensed by the electrodes 306 in FIG. 3B because the electrodes 306 in FIG. 3C do not have as much contact with the cardiac tissue 304C, as shown in FIG. 3C. Furthermore, the ring electrodes 308 may not sense as much voltage corresponding to the cardiac tissue 304C because the ring electrodes are not included in the contact region 314C. According to embodiments, these respective sensed voltages are used to determine a resultant vector and the orientation of the catheter tip assembly, as described below.

Figure 4:
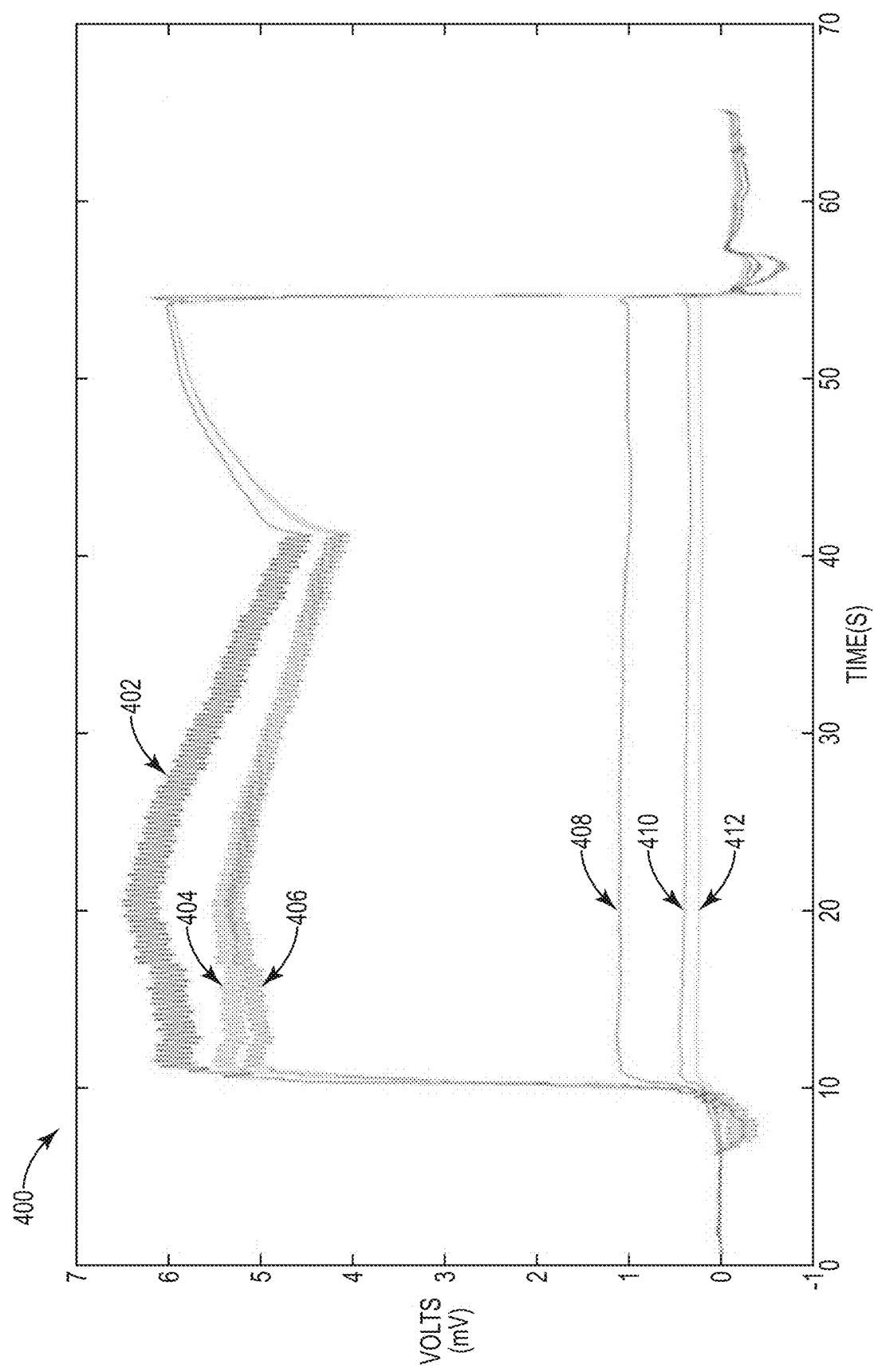
FIG. 4 depicts an illustrative graph of voltages sensed by electrodes, in accordance with embodiments of the disclosure.

FIG. 4 depicts an illustrative graph 400 of voltages sensed by electrodes, in accordance with embodiments of the disclosure. In this example, with reference to the illustrative catheter tip assembly 200 depicted in FIG. 2, the electrodes 208, 212 are sensing voltages while a current is being driven through electrode 206. More specifically, the voltage 402 is the voltage sensed by electrode 208(1); the voltage 404 is the voltage sensed by electrode 208(2), the voltage 406 is the voltage sensed by another mapping electrode 208 (not shown), the voltage 408 is the voltage sensed by electrode 212(1), the voltage 410 is the voltage sensed by electrode 212(2) and the voltage 412 is the voltage sensed by electrode 212(3).

In this example, a catheter was disposed in a cardiac chamber. For approximately 7 seconds, the catheter was contacting blood, while not being in contact with cardiac tissue. In this example, the voltage sensed by the electrodes 208, 212 when in contact with blood has been calibrated to zero volts. As shown, the sensed voltage for the first 7 seconds is approximately zero volts.

At approximately 7 seconds, RF energy is emitted from the electrode 206. RF energy is continued to be emitted from electrode 206 until approximately 40 seconds. From approximately 7 seconds to 10 seconds, the catheter tip assembly heats up due to the RF energy provided by the electrode 206. As a result, the impedance of the catheter tip assembly decreases. Since the RF energy provided remains constant, the sensed voltage decreases due to the impedance decrease.

At approximately 10 seconds, the catheter tip assembly comes into contact with cardiac tissue. The voltage sensed by electrodes 208 increases dramatically during this time because cardiac tissue has a higher impedance than blood. The difference in voltages 402, 404, 406 sensed by electrodes 208 is due to an electrode 208 being in better contact with the cardiac tissue than another electrode 208. For example, the electrode 208(1) that is sensing voltage 402 is in better contact with the cardiac tissue than the electrode 208(2) that is sensing voltage 404. The difference in voltages 402, 404, 406 sensed by the electrodes 208 and the voltages 408, 410, 412 sensed by the ring electrodes 212 is due to the electrodes 208 being closer to, and/or in better contact with, the cardiac tissue than the electrodes 212. The electrodes 208, 212 continue to contact the tissue while the electrode 206 emitted RF energy for approximately 30 seconds. During this time, there is a decrease in the measured voltage due to heating of the catheter tip assembly, as well as due to the cardiac tissue being damaged by the ablation.

At approximately 40 seconds, the electrode 206 stops providing RF energy; however, the electrodes 208, 212 continue to contact the cardiac tissue. During this time, the sensed voltage increases as the catheter tip assembly cools. After approximately 55 seconds, the electrodes 208, 212 no longer contact the cardiac tissue, which is shown by a dramatic decrease in sensed voltage.

In embodiments where a current is provided to all of the electrodes 206, 208, 212 and respective voltages are measured at each of the electrodes 206, 208, 212, forty-nine different voltages are measured.

Figure 5:
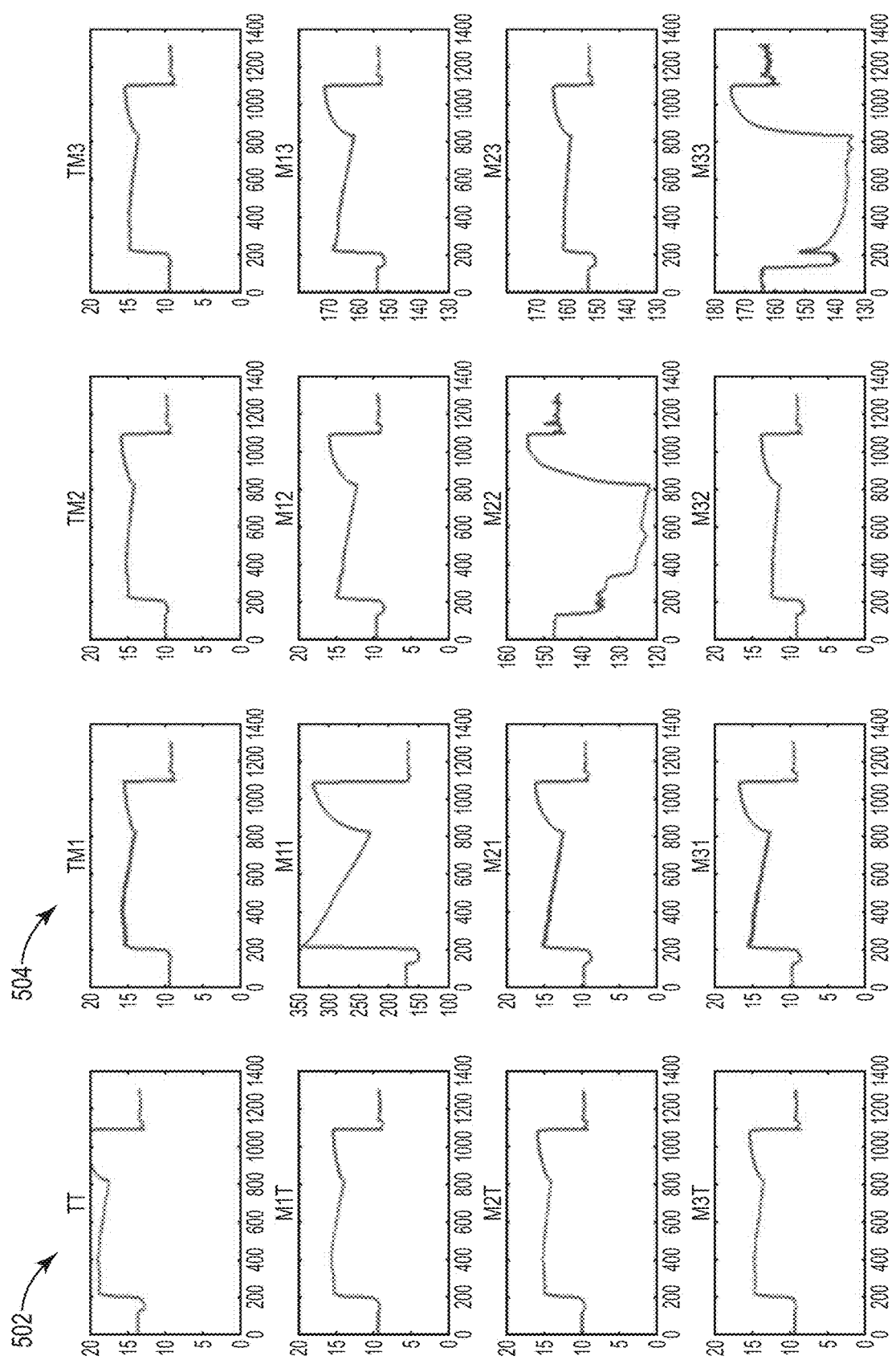
FIG. 5 depicts illustrative graphs of voltages sensed by electrodes, in accordance with embodiments of the disclosure.

FIG. 5 depicts a subset of the forty-nine voltage measurements. Each graph shown in FIG. 5 is annotated by an electrode 206, 208, 212 that a current is being driven through and an electrode 206, 208, 212 at which the voltage is sensed. In this example, the electrode 206 is annotated as "T" and mapping electrodes 208(1), 208(2) are annotated with a "M1" and "M2," respectively. "M3" refers to another mapping electrode 208 located on the distal tip of the tip assembly 202 that is not shown in FIG. 2. As such, graph 502 depicts a current being driven through electrode 206 and a voltage being sensed at electrode 206. As another example, graph 504 depicts a current being provided by electrode 206 and a voltage being measured at electrode 208(1).

In the graphs shown in FIG. 5, a similar sequence of events is being performed, as was being performed in FIG. 4. In particular, for approximately 100 time units, the catheter was contacting blood, while not being in contact with cardiac tissue. At approximately 100 time units, RF energy is emitted from the electrode 206. At approximately 200 time units, the catheter tip assembly comes into contact with cardiac tissue. At approximately 800 time units, the electrode 206 stops providing RF energy; however, the electrodes 208, 212 continue to contact the cardiac tissue. Finally, at approximately 1100 time units, the electrodes 208, 212 no longer contacts the cardiac tissue.

Figure 6:
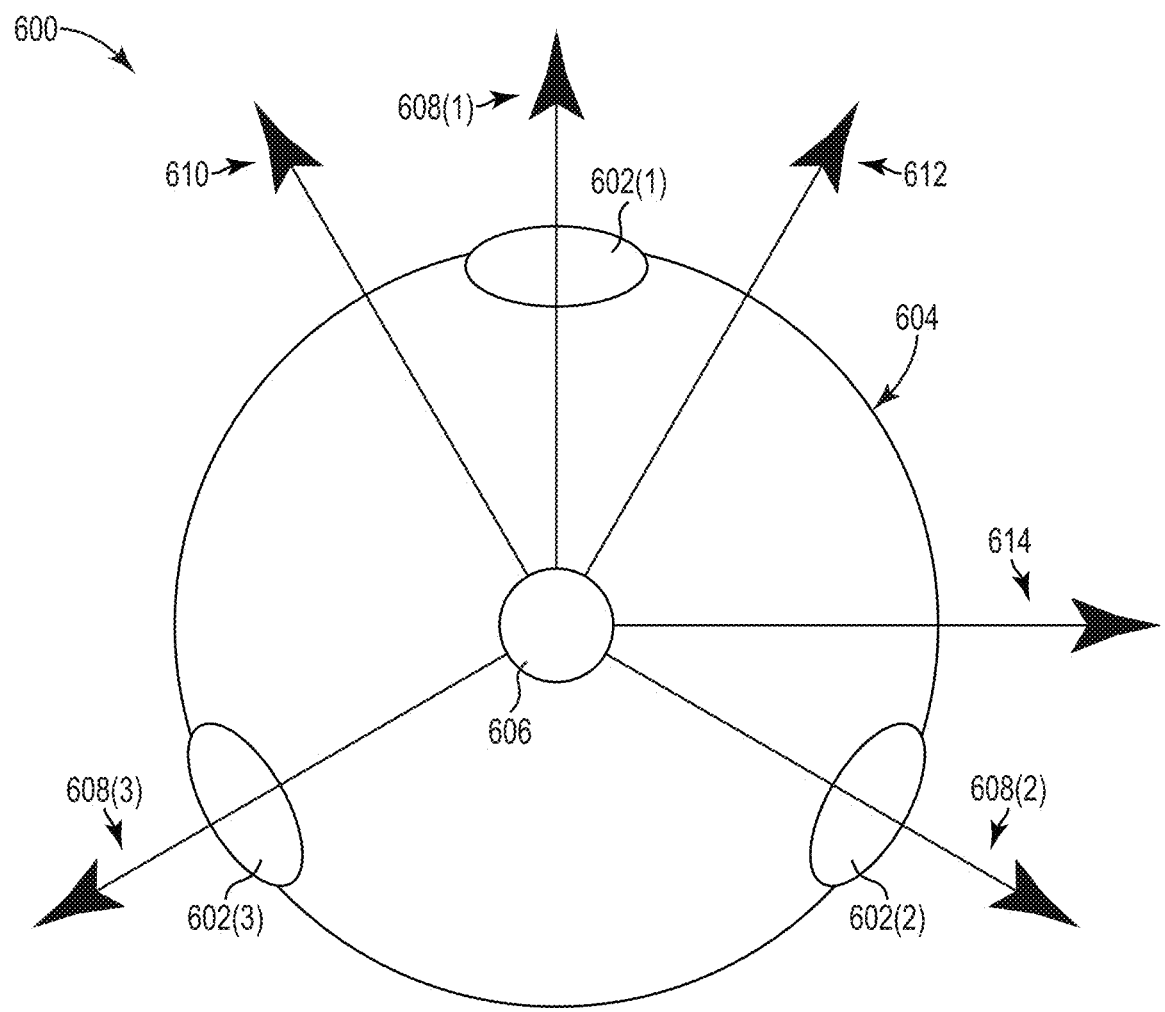
FIG. 6 depicts an illustrative end-on schematic view of a catheter, in accordance with the embodiments of the disclosure.

FIG. 6 depicts an illustrative end-on view of a catheter tip assembly 600, in accordance with the embodiments of the disclosure. In embodiments, the catheter tip assembly 600 may have some or all of the functionality of the catheter tip assemblies 104, 202 shown in FIGS. 1 and 2, respectively. In embodiments where the catheter tip assembly 600 is the catheter tip assembly 202 shown in FIG. 2, the illustrative end-on view may be a cross-sectional view along line 6-6 of FIG. 2.

The catheter tip assembly 600 includes a plurality of mapping electrodes 602. In embodiments, the mapping electrodes 602 include three mapping electrodes 602(1), 602(2), 602(3), distributed along a circumference of the exterior wall 604 of the catheter 600. In other embodiments, the catheter tip assembly 600 may have more mapping electrodes 602 or fewer mapping electrodes 602 than shown in FIG. 6. In embodiments, the three mapping electrodes 602(1), 602(2), 602(3) are evenly distributed along a circumference of the exterior wall 604. The mapping electrodes 602 may have some or all of the same functionality as the mapping 106, 208 shown in FIGS. 1 and 2, respectively. As such, the mapping electrodes 602 may provide current into a patient's body and sense electrical activity, as described above in relation to FIGS. 1 and 2. In embodiments, the electrical activity sensed is a voltage.

While sensing electrical activity, the positions of each of the mapping electrodes 602 may be determined. Accordingly, position coordinates may be associated with the sensed electrical activity. Since the catheter may be moving, the position coordinates may be a function of time. Using the respective position coordinates for the electrodes 602, a mean or median of the position coordinates at a point in time may be calculated. The mean or median position may be represented as a virtual electrode 606. In embodiments, the position of the virtual electrode 606 is used as an origin for the vectors corresponding to each electrode 602. As such, sensed electrical activity by an electrode may correspond to a vector that originates at the virtual electrode 606 and has a direction towards the electrode 602 that sensed the electrical activity. As an example, assume each of the electrodes 602 sense the same voltage at a point in time. As such, vectors 608 corresponding to the sensed voltages may be drawn from the virtual electrode 606 to each of the electrodes 602, as shown in FIG. 6. In other embodiments, the vectors 606 may have an origin other than the virtual electrode 606. For example, one of the electrodes 602 may be used as an origin for the vectors 608.

The magnitude of the vectors 608 may correspond to the magnitude of the sensed electrode signal. As described above, if the sensed electrical signal is sensed voltage, the magnitude of the sensed voltage may correspond to whether the electrode 602 is in contact with cardiac tissue. That is, the higher the voltage, the more likely the electrode 602 is in contact with cardiac tissue because cardiac tissue has a higher impedance than blood. Additionally, voltage magnitude may also correspond to how hard the electrode 602 is pushing into cardiac tissue. That is, if two electrodes 602(1), 602(2) are contacting cardiac tissue and electrode 602(1) is exerting a higher force on the cardiac tissue, then electrode 602(1) may sense a higher voltage. All the vectors 608 shown in FIG. 6 have approximately the same length. As a result, the voltages sensed by the electrodes 606 were approximately the same.

In embodiments, the virtual electrode 606 may also be a mean or median of the magnitudes of the sensed electrical signals by the electrodes 602. In these embodiments, the vectors 608 may correspond the difference between electrical signal sensed at an electrode 602 and the virtual electrode 606. For example, the vector 608(1) may be equal to the difference between the magnitude of the electrical signal for the virtual electrode 606 (i.e., the mean or median of the magnitudes of the sensed electrical signals for all the electrodes) and the magnitude of the electrical signal for the electrode 602(1).

Furthermore, in embodiments, a difference between the vectors 608 may be determined. As examples, the vector 610 corresponds to the difference between the vector 608(1) and the vector 608(2); the vector 612 corresponds to the difference between the vector 608(1) and the vector 608(3); and, the vector 614 corresponds to the difference between the vector 608(2) and the vector 608(3). Each of these vectors may be used in determining a resultant vector, as described below.

In embodiments that include more than three electrodes 602, the electrodes may be non-planar. For example, an electrode may be located on the tip of the catheter where the virtual electrode 606 is positioned. In these embodiments, three-dimensional vectors may be determined. For example, if an electrode where located on the tip of the catheter, vector pointing in different directions in a hemisphere may be determined.

FIGS. 7A-7F depict determined resultant vectors 702A-702F, as a function of time, in accordance with embodiments of the disclosure. In this example, a catheter tip assembly is disposed in a cardiac chamber. The catheter tip assembly has an electrode configures that is similar to the tip assemblies 104, 202 shown in FIGS. 1 and 2. In particular, the catheter tip assembly has three electrodes, which are disposed circumferentially around the catheter tip assembly. After the catheter tip assembly is disposed in a cardiac chamber, the catheter tip assembly is repositioned around the cardiac chamber so that the electrodes on the catheter tip assembly contact the cardiac tissue at different times and in different manners. The voltages sensed by the electrodes, as a function of time, are shown in graphs 704(1), 704(2), 704(3), respectively. Each graph 704(1), 704(2) 704(3) includes a line 706A-706F that indicates the respective time at which the resultant vector 702A-702F being displayed is being determined. The electrodes corresponding to each graph may be referred to hereafter as the reference number that is assigned to the respective graph for the electrode. For example, the electrode with the corresponding graph 704(1) may be referred to as electrode 704(1).

The magnitude of a resultant vectors 702A-702F is the sum of the voltage magnitudes shown in graphs 704(1), 704(2), 704(3) at a respective time 706A-706F. The direction of a resultant vectors 702A-702F is determined by the contribution from each electrode 704 to the magnitude of the resultant vector 702A-702F. For example, if electrode 704 (1) is the sole contributor to the magnitude of the resultant vector 702A-702F, then the resultant vector 702A-702F may point in the direction of the electrode 704(1). If, however, both electrodes 704(1) and 704(2) contribute equally to the magnitude of the resultant vector 702A-702F, then the resultant vector 702A-702F may point to a direction that is in between the electrodes 704(1) and 704(2). From the resultant vectors 702A-702F, one may determine the orientation of the catheter with respect to cardiac tissue, as described below.

Figure 7A:
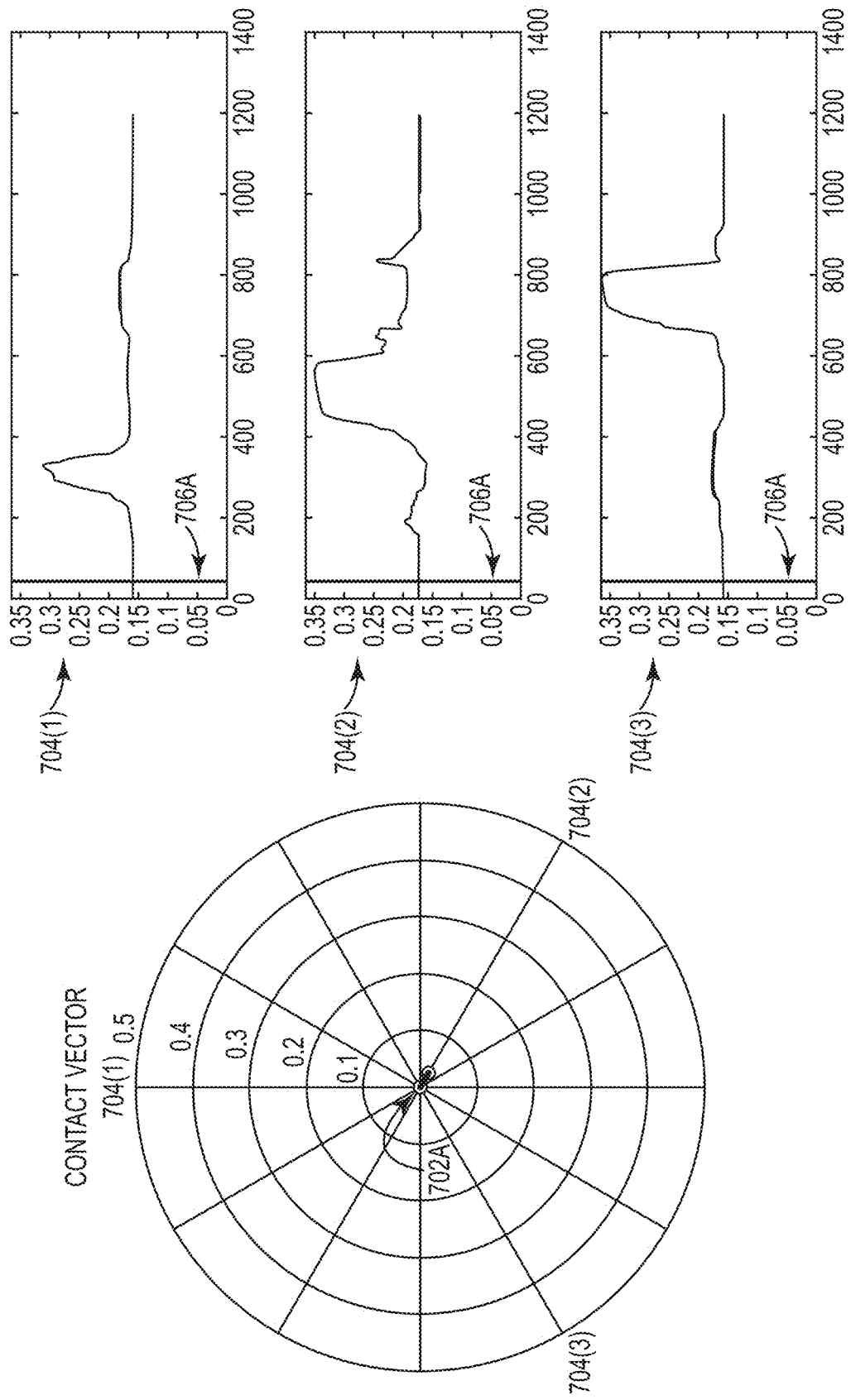
FIGS. 7A-7F depict resultant vectors 802A-802F, determined as a function of time, in accordance with embodiments of the disclosure.

Referring to FIG. 7A, there is a very small resultant vector 702A at time 706A pointing in the direction of electrode 704(2). The resultant vector 702A is small because the voltages sensed by the electrodes 704 are very small, as shown in graphs 704. Since the resultant vector 702A is very small, it is likely that none of the electrodes 704 are in contact with the cardiac tissue. This resultant vector 702A may correspond to either the catheter not being in contact with cardiac tissue or the catheter being oriented with respect to the cardiac tissue as shown in FIG. 3A. In either case, a user may know to adjust the orientation of the catheter tip assembly to either make contact with the cardiac tissue or possibly change the orientation of the catheter tip assembly with respect to the cardiac tissue for the reasons discuss above in FIG. 3A.

Figure 7B:
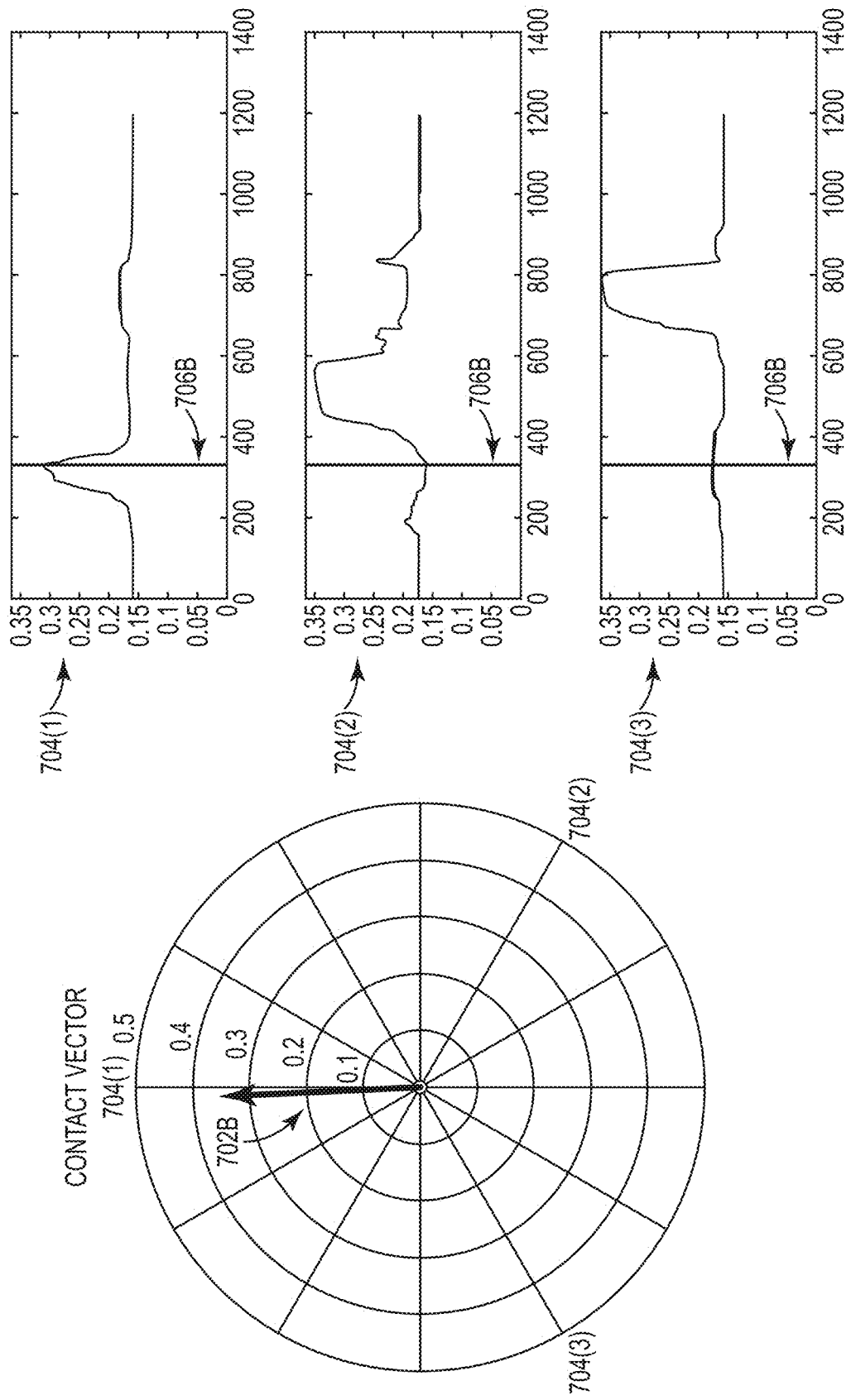

Referring to FIG. 7B, a resultant vector 702B is pointing in the direction of electrode 704(1). Furthermore, the magnitude of the resultant vector 702B is somewhat large. Since the resultant vector 702B is pointing in the direction of the electrode 704(1), it is likely the electrode 704(1) is in contact with the cardiac tissue and the electrodes 704(2), 704(3) are not in contact with the cardiac tissue. Since the electrode 704(1) is contacting the cardiac tissue and since both electrodes 704(2) and 704(3) are not contacting the cardiac tissue, one may determine that the orientation of the catheter tip assembly with respect to the cardiac tissue is approximately the orientation shown in either FIG. 3B or FIG. 3C, assuming the catheter tip assembly has an electrode configuration similar to the electrode configuration of the mapping electrodes 106, 208 shown in FIGS. 1 and 2, respectively. If the catheter includes mapping ring electrodes, such as the mapping ring electrodes 212 shown in FIG. 2, then one may determine whether the orientation of the catheter tip assembly with respect to the cardiac tissue is more similar to FIG. 3B or FIG. 3C by sensing a voltage at a mapping ring electrode. If the voltage sensed by mapping ring electrode corresponds to contact with cardiac tissue, then one may determine the catheter has an orientation similar to the orientation shown in FIG. 3B. If, however, the mapping ring electrode senses a voltage that corresponds to a voltage that is commonly sensed in blood, then one may determine the catheter has an orientation similar to the orientation shown in FIG. 3C. If a catheter tip assembly that does not include mapping ring electrodes is being used, one may want to reposition the catheter tip assembly under the resultant vector is similar to the resultant vector 702D shown n FIG. 7D.

Figure 7C:
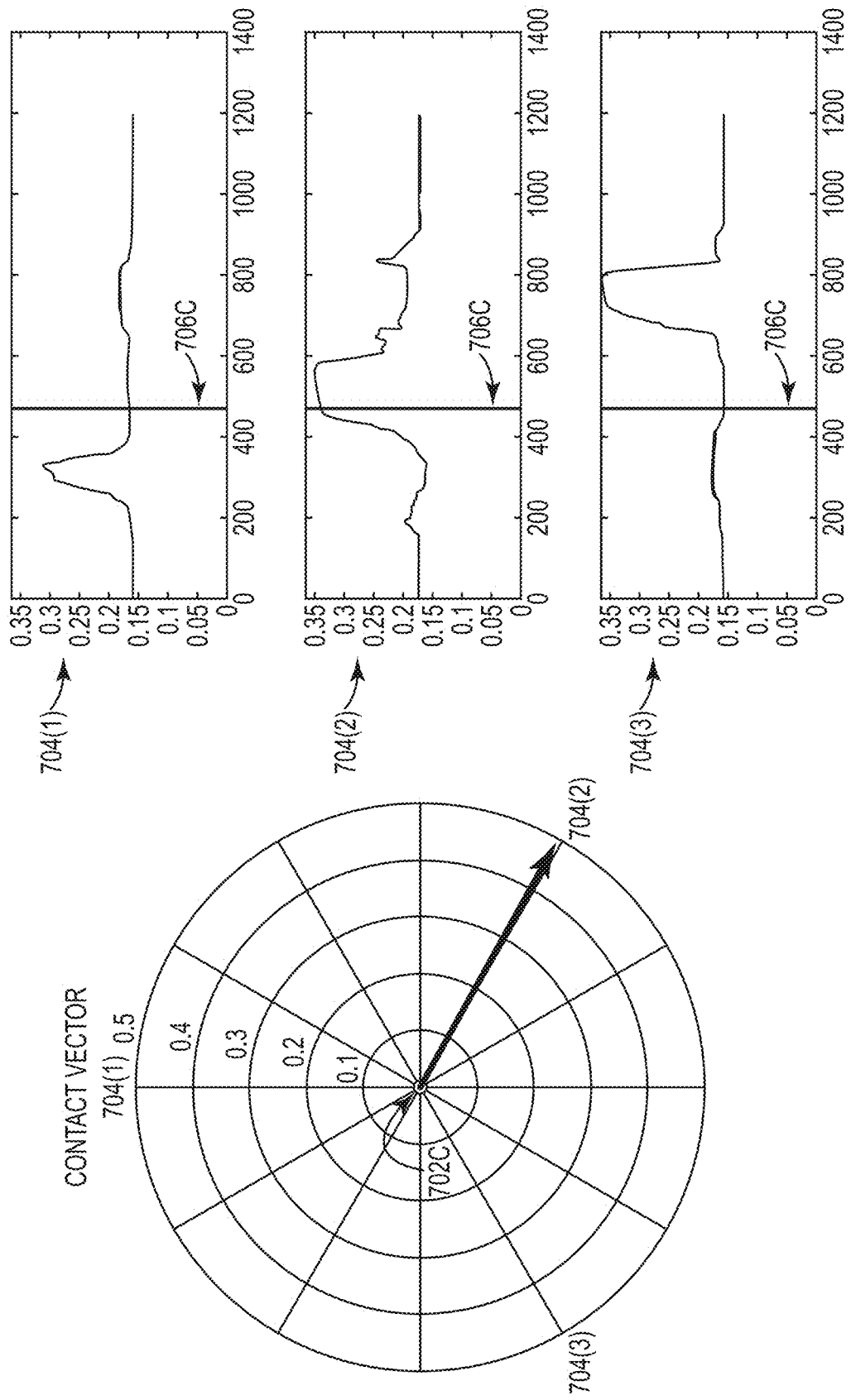

Referring to FIG. 7C, a resultant vector 702C is pointing in the direction of electrode 704(2). Furthermore, the magnitude of the resultant vector 702C is somewhat large. Since the resultant vector 702C is pointing in the direction of the electrode 704(2), it is likely the electrode 704(2) is in contact with the cardiac tissue and the electrodes 704(1), 704(3) are not in contact with the cardiac tissue. Since the electrode 704(2) is contacting the cardiac tissue and since both electrodes 704(1) and 704(3) are not contacting the cardiac tissue, one may determine that the orientation of the catheter tip assembly with respect to the cardiac tissue is approximately the orientation shown in either FIG. 3B or FIG. 3C, assuming the catheter tip assembly has an electrode configuration similar to the electrode configuration of the mapping electrodes 106, 208 shown in FIGS. 1 and 2, respectively. Similar to above, if the catheter includes mapping ring electrodes, such as the mapping ring electrodes 212 shown in FIG. 2, then one may determine whether the orientation of the catheter tip assembly with respect to the cardiac tissue is more similar to FIG. 3B or FIG. 3C by sensing a voltage at a mapping ring electrode. If the voltage sensed by mapping ring electrode corresponds to contact with cardiac tissue, then one may determine the catheter has an orientation similar to the orientation shown in FIG. 3B. If, however, the mapping ring electrode senses a voltage that corresponds to a voltage that is commonly sensed in blood, then one may determine the catheter has an orientation similar to the orientation shown in FIG. 3C. If a catheter tip assembly that does not include mapping ring electrodes is being used, one may want to reposition the catheter tip assembly under the resultant vector is similar to the resultant vector 702D shown n FIG. 7D.

Figure 7D:
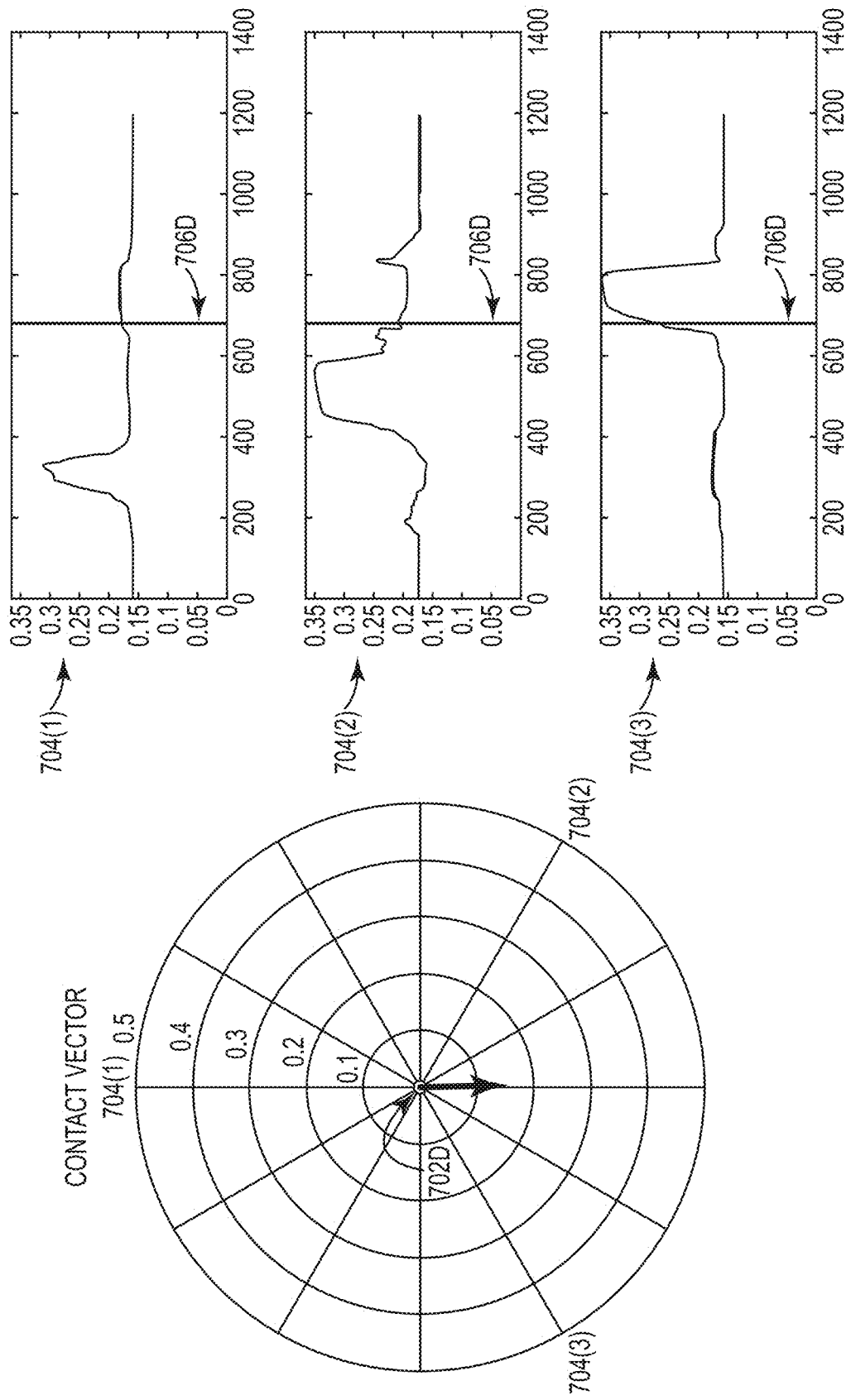

Referring to FIG. 7D, a resultant vector 702D is pointing to a direction that is between electrodes 704(2) and 704(3). The magnitude of the resultant vector 702C is larger than if the electrodes 704(2), 704(3) were sensing blood, but smaller than magnitudes shown in FIGS. 7B, 7C and 7E. As such, it is likely that both electrodes 704(2), 704(3) are in contact with the cardiac tissue and the electrode 704(1) is not in contact with the cardiac tissue. Since the electrodes 704(2), 704(3) are contacting the cardiac tissue and electrode 704(1) is not contacting the cardiac tissue, one may determine that the orientation of the catheter tip assembly with respect to the cardiac tissue is approximately the orientation shown in either FIG. 3B or 3C, assuming the catheter tip assembly has an electrode configuration similar to the electrode configuration of the mapping electrodes 106, 208 shown in FIGS. 1 and 2, respectively. However, since the magnitude of the determined vector 702D is not as large as magnitudes shown in FIGS. 7B, 7C and 7E, one may determine that the angle of a normal of the catheter tip assembly is likely larger than 90 degrees, otherwise the electrodes 704(2), 704(3) would likely sense a higher voltage. As such, one may determine the orientation of the catheter tip assembly with respect to the cardiac tissue is approximately the orientation shown in FIG. 3C, which may be a preferred orientation for the reasons stated above with respect to FIG. 3C.

Figure 7E:
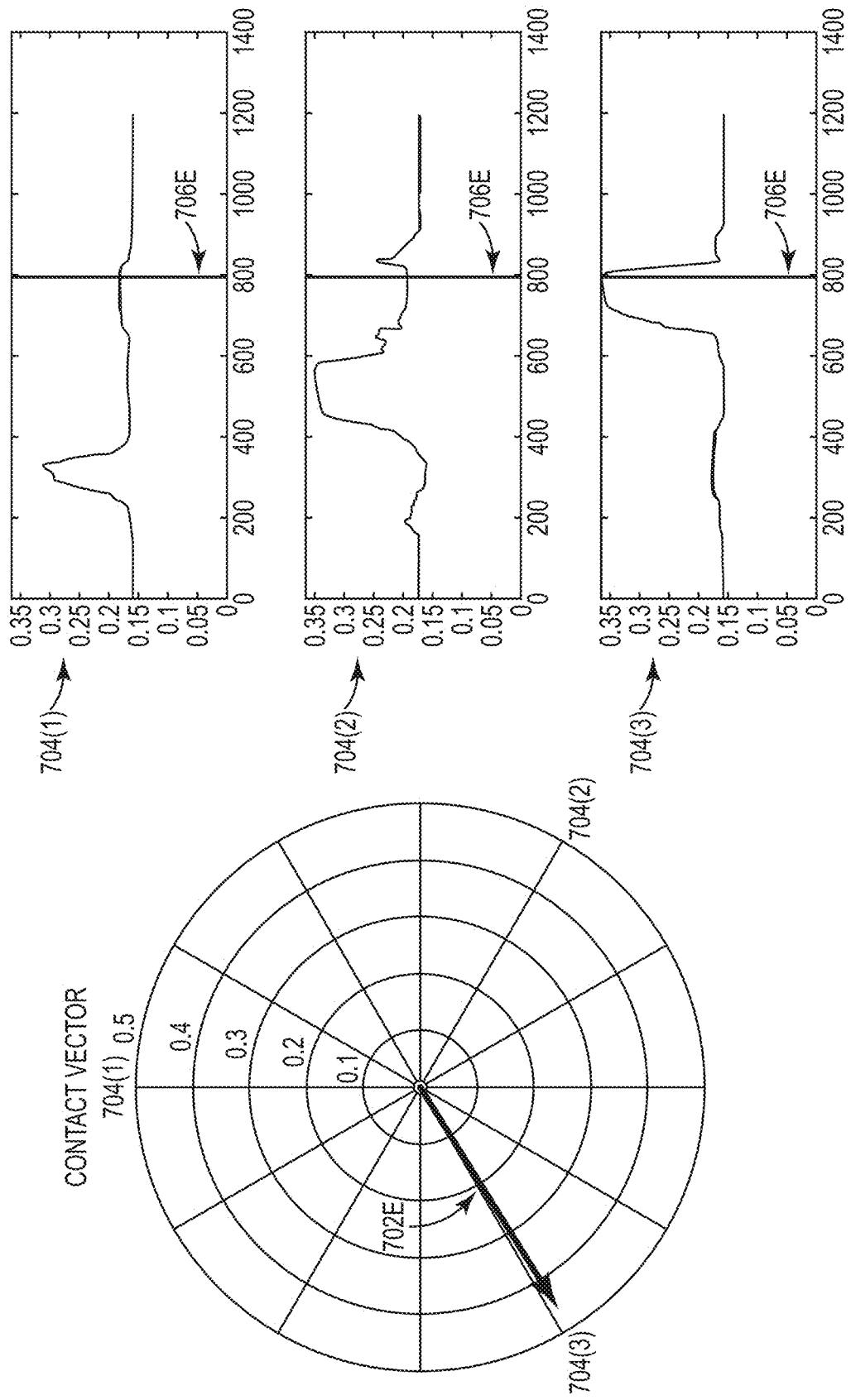

Referring to FIG. 7E, a resultant vector 702E is pointing in the direction of electrode 704(3). Furthermore, the magnitude of the resultant vector 702E is somewhat large. Since the resultant vector 702E is pointing in the direction of the electrode 704(3), it is likely the electrode 704(3) is in contact with the cardiac tissue and the electrodes 704(1), 704(2) are not in contact with the cardiac tissue. Since the electrode 704(3) is contacting the cardiac tissue and since both electrodes 704(1) and 704(2) are not contacting the cardiac tissue, one may determine that the orientation of the catheter tip assembly with respect to the cardiac tissue is approximately the orientation shown in either FIG. 3B or FIG. 3C, assuming the catheter tip assembly has an electrode configuration similar to the electrode configuration of the mapping electrodes 106, 208 shown in FIGS. 1 and 2, respectively. Similar to above, if the catheter includes mapping ring electrodes, such as the mapping ring electrodes 212 shown in FIG. 2, then one may determine whether the orientation of the catheter tip assembly with respect to the cardiac tissue is more similar to FIG. 3B or FIG. 3C by sensing a voltage at a mapping ring electrode. If the voltage sensed by mapping ring electrode corresponds to contact with cardiac tissue, then one may determine the catheter has an orientation similar to the orientation shown in FIG. 3B. If, however, the mapping ring electrode senses a voltage that corresponds to a voltage that is commonly sensed in blood, then one may determine the catheter has an orientation similar to the orientation shown in FIG. 3C. If a catheter tip assembly that does not include mapping ring electrodes is being used, one may want to reposition the catheter tip assembly under the resultant vector is similar to the resultant vector 702D shown n FIG. 7D.

Figure 7F:
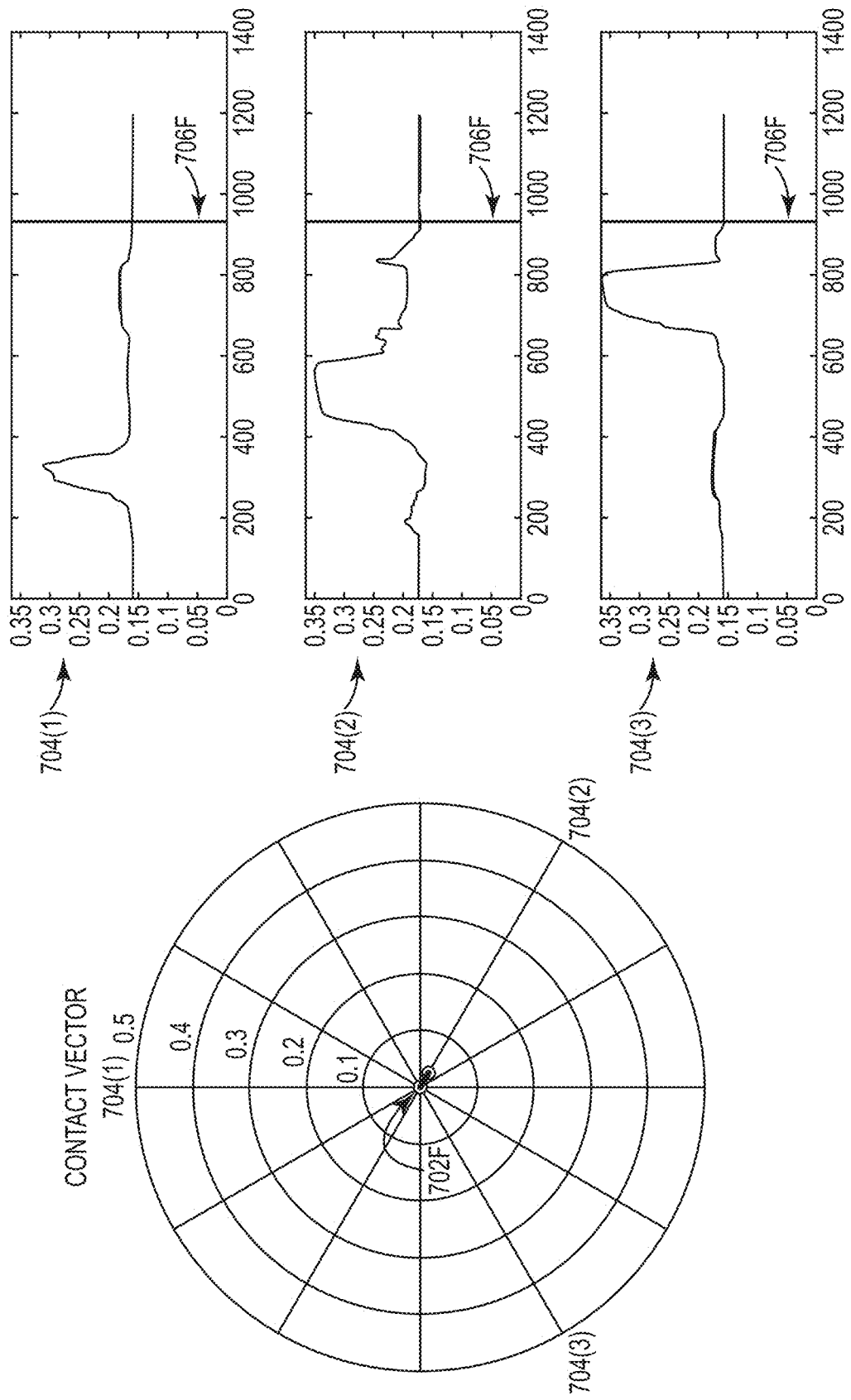

Referring to FIG. 7F, similar to FIG. 7A, there is a very small resultant vector 702F at time 706F pointing in the direction of electrode 704(2). Again, the resultant vector 702F it is likely that none of the electrodes 704 are in contact with the cardiac tissue. As such, this resultant vector 702F may correspond to either the catheter not being in contact with cardiac tissue or the catheter being oriented with respect to the cardiac tissue as shown in FIG. 3A. In either case, a user may know to adjust the orientation of the catheter tip assembly to either make contact with the cardiac tissue or possibly change the orientation of the catheter tip assembly with respect to the cardiac tissue for the reasons discuss above in FIG. 3A.

Figure 8:
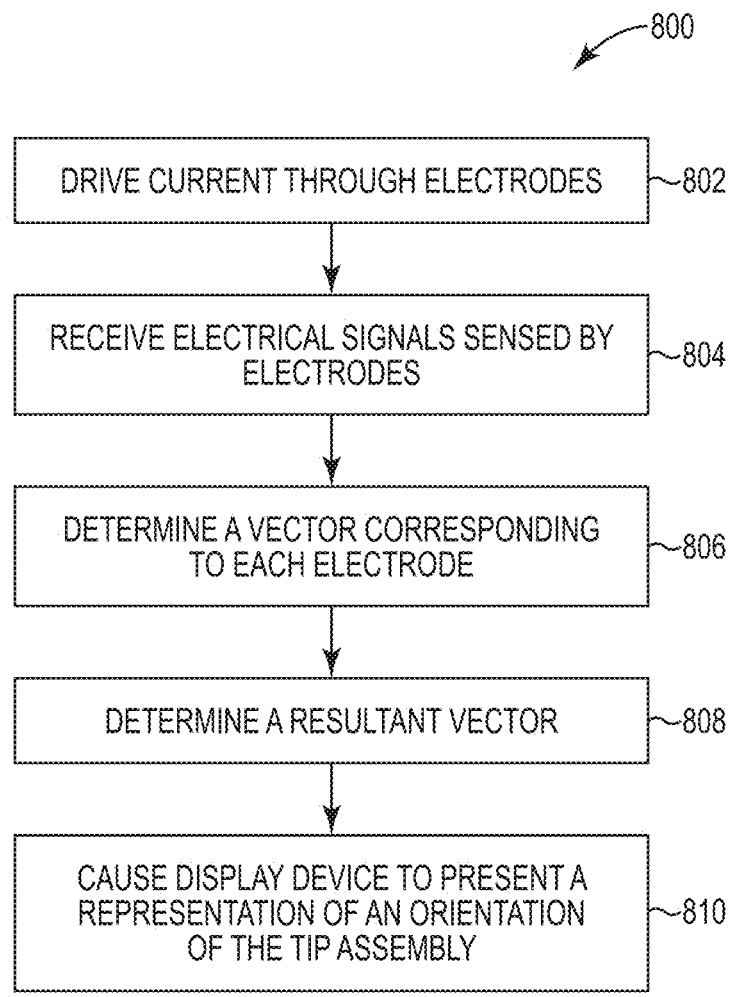
FIG. 8 is a flow diagram depicting an illustrative method of determining an orientation of a tip assembly of a catheter, in accordance with embodiments of the disclosure.

FIG. 8 is a flow diagram depicting an illustrative method 800 of determining an orientation of a tip assembly of a catheter, in accordance with embodiments of the disclosure. Method 800 includes driving a current through one or more electrodes (block 802). In embodiments, the tip assembly of the catheter may be similar to the tip assemblies 104, 206 discuss in relation to FIGS. 1 and 2, respectively. In embodiments, the current provided to one or more of the electrodes may be a sub-threshold current, wherein a sub-threshold current is a current that is less than a current that is required to ablate cardiac tissue. As such, a user of catheter may determine if the tip assembly of the catheter is oriented in a preferred manner, as described in more detail below, before ablating cardiac tissue. The sub-threshold current may be provided by, for example, the sub-threshold frequency generator 132 in FIG. 1, and may have a frequency on the order of 10 kHz. Other frequencies may be used as well. For example, a current that is capable of ablating tissue may also be used.

Method 800 also includes receiving electrical signals sensed by one or more electrodes (block 804). In embodiments, the one or more electrodes that sense electrical signals may be the same one or more electrodes in block 802. In embodiments, the sensed electrical signals include voltage. As discussed above, when sensing voltage within a cardiac chamber, a higher voltage may indicate that the catheter tip assembly is in contact with cardiac tissue rather than being in contact with blood since cardiac tissue has a higher impedance than blood, as will be readily understood by those skilled in the art.

Method 800 also includes determining a vector corresponding to each electrode (block 806). In embodiments, a vector corresponding to each electrode can be determined as described above in relation to FIG. 6. The vector corresponding to each electrode may comprise determining a magnitude and direction for vector. In embodiments, the magnitude and direction of the vector may be determined as described in relation to FIG. 6 above. For example, a mean or median of the positions and the electrical signals sensed at each electrode may be determined. The mean or median may be used as the origin of a vector for an electrode. In these embodiments, the direction of the vector may be from the origin to the electrode and the magnitude may be the magnitude of the sensed electrical signal.

Method 800 also includes determining a resultant vector (block 808). In embodiments, the resultant vector may be determined as described above in relation to FIGS. 6 and 7. For example, a resultant vector may be determined by summing the determined vectors in block 806. In embodiments, the resultant vector is indicative of an orientation of the tip assembly, as described above in relation to FIG. 7.

Method 800 also includes causing a display device to present a representation of an orientation of the tip assembly (block 810). Example representations of tip assemblies are shown in FIGS. 3A-3C. In embodiments, the representation of the orientation of the tip assembly may include a graphical depiction o of the resultant vector determined in block 808. The display device may have some or all of the characteristics of the display device 142 shown in FIG. 1.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A catheter system, comprising:
a catheter comprising a tip assembly, the tip assembly having a plurality of electrodes, the plurality of electrodes configured to measure electrical signals of an anatomical surface; and
a processing unit configured to:
receive a first electrical signal sensed by a first electrode of the plurality of electrodes and a second electrical signal sensed by a second electrode of the plurality of electrodes;
determine a first vector, based on the first electrical signal, corresponding to the first electrode;

determine a second vector, based on the second electrical signal, corresponding to the second electrode; and determine a resultant vector by summing at least the first vector and the second vector, wherein the resultant vector is indicative of which portion of the tip assembly is contacting the anatomical surface and an orientation of the tip assembly relative to the anatomical surface, wherein the orientation is an angle between a normal vector extending from a distal end of the tip assembly and the anatomical surface producing the first electrical signal and the second electrical signal.

2. The catheter system of claim 1, the processing unit further configured to cause the first and second electrodes to provide a first and second current into a patient's body, respectively.

3. The catheter system of claim 1, the first vector comprising a first magnitude and a first direction, and the second vector comprising a second magnitude and a second direction, wherein the first and second directions correspond, respectively, to a first and second position relative to a central terminal.

4. The catheter system of claim 3, wherein the first and second magnitudes comprise a first and second voltage, respectively.

5. The catheter system of claim 1, further comprising a display device operatively coupled to the processing unit, wherein the processing unit is configured to cause the display device to present a representation of the orientation of the tip assembly.

6. The catheter system of claim 5, wherein the representation of the orientation of the tip assembly comprises a graphical depiction of the resultant vector.

7. The catheter system of claim 1, the tip assembly further comprising an exterior wall configured to deliver radio frequency (RF) energy for an RF ablation procedure, the plurality of electrodes comprising a plurality of mapping electrodes evenly distributed along a circumference of the exterior wall.

8. An ablation catheter system, comprising:
a catheter comprising:
a tip assembly that includes a conductive exterior wall for delivering radio frequency (RF) energy for an RF ablation procedure, and a plurality of mapping electrode openings; and
a plurality of mapping electrodes, positioned in the plurality of mapping electrode openings, the plurality of mapping electrodes configured to measure electrical signals of an anatomical surface; and
a processing unit configured to:
drive a first current through a first mapping electrode of the plurality of mapping electrodes and a second current through a second mapping electrode of the plurality of mapping electrodes;
receive a first electrical signal sensed by the first mapping electrode and a second electrical signal sensed by the second mapping electrode;
determine a first vector, based on the first electrical signal, corresponding to the first mapping electrode;
determine a second vector, based on the second electrical signal, corresponding to the second mapping electrode; and
determine a resultant vector by summing at least the first vector and the second vector, wherein the resultant vector is indicative of which portion of the tip assembly is contacting the anatomical surface and an orientation of the tip assembly relative to the anatomical surface, wherein the orientation is an angle between a normal vector extending from a distal end of the tip assembly and the anatomical surface producing the first electrical signal and the second electrical signal.

9. The ablation catheter system of claim 8, the first vector comprising a first magnitude and a first direction, and the second vector comprising a second magnitude and a second direction, wherein the first and second directions correspond, respectively, to a first and second position relative to a central terminal.

10. The ablation catheter system of claim 9, wherein the central terminal comprises a virtual electrode that represents a vector summation based on vectors associated with all of the plurality of mapping electrodes.

11. The ablation catheter system of claim 9, wherein the first and second magnitudes comprise a first and second voltage, respectively.

12. The ablation catheter system of claim 9, wherein the first and second magnitudes comprise a first and second impedance, respectively.

13. The ablation catheter system of claim 8, further comprising a display device operatively coupled to the processing unit, wherein the processing unit is configured to cause the display device to present a representation of the orientation of the tip assembly.

14. The ablation catheter system of claim 13, wherein the representation of the orientation of the tip assembly comprises a graphical depiction of the resultant vector.

15. A method of determining an orientation of a tip assembly of an ablation catheter relative to an anatomical surface, the tip assembly comprising a conductive exterior wall configured to deliver radio frequency (RF) energy for an RF ablation procedure, and a plurality of mapping electrodes evenly distributed along a circumference of the exterior wall, the method comprising:
driving a first current through a first mapping electrode of the plurality of mapping electrodes;
driving a second current through a second mapping electrode of the plurality of mapping electrodes;
receiving a first electrical signal sensed by the first mapping electrode;
receiving a second electrical signal sensed by the second mapping electrode;
determining a first vector, based on the first electrical signal, corresponding to the first mapping electrode;
determining a second vector, based on the second electrical signal, corresponding to the second mapping electrode;
determining a resultant vector by summing at least the first vector and the second vector, wherein the resultant vector is indicative of which portion of the tip assembly is contacting the anatomical surface and an orientation of the tip assembly relative to the anatomical surface, wherein the orientation is an angle between a normal vector extending from a distal end of the tip assembly and the anatomical surface producing the first electrical signal and the second electrical signal; and
causing a display device to present a representation of the orientation of the tip assembly.

16. The method of claim 15, wherein the representation of the orientation of the tip assembly comprises a graphical depiction of the resultant vector.

17. The method of claim 15, wherein determining the first vector and the second vector comprises determining a first magnitude and a first direction, and a second magnitude and a second direction, respectively, wherein the first and second directions correspond, respectively, to a first and second position relative to a central terminal.

18. The method of claim 17, wherein the first and second magnitudes comprise a first and second voltage, respectively.

19. The method of claim 17, wherein the central terminal comprises a virtual electrode that represents a vector summation based on vectors associated with all of the plurality of mapping electrodes.

20. The method of claim 17, further comprising driving RF energy through the exterior wall for an RF ablation procedure; and filtering the first and second electrical signals to remove an RF component from each.

* * * * *